US00PP09397P

United States Patent [19]

Zary

[11] Patent Number: Plant 9,397

[45] Date of Patent: Dec. 12, 1995

[54] HYBRID TEA ROSE PLANT NAMED 'JACHEIR'

[75] Inventor: Keith W. Zary, Thousand Oaks, Calif.

[73] Assignee: Bear Creek Gardens, Inc., Medford, Oreg.

[21] Appl. No.: 281,252

[22] Filed: Jul. 26, 1994

[51] Int. Cl.[6] ..... A01H 5/00

[52] U.S. Cl. ..... Plt./21

[58] Field of Search ..... Plt./19, 11, 20, Plt./21

*Primary Examiner*—Howard J. Locker

*Attorney, Agent, or Firm*—Klarquist Sparkman Campbell Leigh & Whinston

[57] ABSTRACT

A hybrid tea rose plant having deep red-purple flowers of good hybrid tea form, strong fragrance, glossy green foliage and excellent plant vigor.

1 Drawing Sheet

The present invention relates to a new and distinct variety of rose plant of the hybrid tea class which was originated by me by crossing an unnamed seedling with the variety "Heirloom" (U.S. Plant Pat. No. 3,234).

The primary objective of this breeding was to produce a new rose variety having the good bud form, vigor and disease resistance of the female unnamed, lavender pink, hybrid tea seedling combined with the deep lavender purple flower color and fragrance of the hybrid tea male parent "Heirloom." The objective was substantially achieved, along with other desirable improvements, as evidenced by the following unique combination of characteristics that are outstanding in the new variety and that distinguish it from its parents, as well as from all other varieties of which I am aware:

1. Deep red-purple flowers of good form;
2. Strong fragrance;
3. Glossy green foliage; and
4. Excellent vigor.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—An unnamed seedling.

*Pollen parent.*—"Heirloom" (U.S. Plant Pat. No. 3,234).

Classification:

*Botanical.*—*Rosa hybrida.*

*Commercial.*—Hybrid tea.

FLOWER

Observations made from specimens grown in a garden environment at Somis, Calif., in March through October, 1993.

Blooming habit: Recurrent.

Bud:

*Size.*—1½ inches long when the petals start to unfurl.

*Form.*—The bud form is pointed ovoid.

*Color.*—When sepals first divide, bud color is Red-Purple Group 59A. When half blown, the upper sides of the petals are Red-Purple Group 59A; and the lower sides of the petals are Red-Purple Group 59C.

*Sepals.*—Color: Green Group 138C. Surface texture: Covered in fine hairs. There are three normally appendaged sepals. There are two unappendaged sepals with hairy edges.

*Receptacle.*—Color: Green Group 137B. Shape: Funnel. Size: Medium (⅝ inch× ⅝ inch). Surface: Smooth.

*Peduncle.*—Length: Short (2½ to 3 inches). Surface: Glandular. Color: Medium green and bronzy when exposed to direct sunlight. Strength: Stiff, erect.

Bloom:

*Size.*—Large. Average open size is 4 to 4½ inches.

*Borne.*—Singly.

*Stems.*—Medium. Average length is about 14 to 18 inches.

*Form.*—When first open: High centered. Permanence: Flattens, outer petals curl back.

*Petalage.*—Number of petals under normal conditions: 25 to 30.

*Color.*—The upper side of the petals is Red-Purple Group 59A. The reverse side of the petals is Red-Purple Group 59C. The base of each petal has a small (¼ inch×¼ inch) white half-moon at the point of attachment. The major color on the upper side is Red-Purple Group 59A.

*Variegations.*—Occasional white flecking on petals.

*Discoloration.*—No change in the general tonality at the end of the first day or at the end of the third day; on day 4 there is fading to red-purple group 59B.

*Fragrance.*—Strong.

Petals:

*Texture.*—Thick.

*Shape.*—Deltoid.

*Form.*—Tips slightly recurved.

*Arrangement.*—Imbricated, with few petaloids in the center.

*Persistence.*—Hang on and dry.

*Lastingness.*—On the plant: Fair (5 days). As a cut flower: Fair (6 or 7 days).

Reproductive parts:

*Anthers.*—Size: Medium. Quantity: Many. Color: Yellow. Arrangement: Regular around styles.

*Filaments.*—Color: Yellow.

*Pollen.*—Color: Lemon yellow.

*Styles.*—Color: Red.

*Stigmas.*—Color: Yellow.

Form: Bush.

Growth: Vigorous, upright, branching. After one full year of growth, plant will be four feet tall and three to three-and-one-half feet in width.

Foliage: Number of leaflets on normal mid-stem leaves: 5 or 7.

*Size.*—Large (5 inches×3½ inches).

*Quantity.*—Abundant.

*Color.*—New foliage: Greyed-Purple Group 183A (upper) and Greyed-Purple Group 183D (lower). Old foliage: Upper surface: Green Group 136B. Lower surface: Green Group 139B.

Leaflets:

*Shape.*—Pointed oval.

*Texture.*—Upper side: Leathery, glossy.

*Edge.*—Serrated.

*Serration.*—Single, small.

*Petiole rachis.*—Color: Green.

*Petiole underside.*—Smooth, with some glands.

*Stipules.*—Short, bearded.

*Disease resistance.*—Resistant to mildew and rust under normal growing conditions at Somis, Calif.

Wood:

*New wood.*—Color: Light green, with some reddish cast. Bark: Smooth.

*Old wood.*—Color: Green. Bark: Smooth.

Prickles:

*Quantity.*—On main canes from base: Ordinary. On laterals from main canes: Ordinary.

*Form.*—Medium (⅛ inch).

*Color when young.*—Red.

Small prickles:

*Quantity.*—On main stalks: Few. On laterals: Few.

*Color.*—Brown.

I claim:

1. A new and distinct variety of rose plant of the hybrid tea class, substantially as herein shown and described, characterized particularly as to novelty by the unique combination of its deep red-purple flowers of good hybrid tea form, strong fragrance, glossy green foliage and excellent plant vigor.

* * * * *

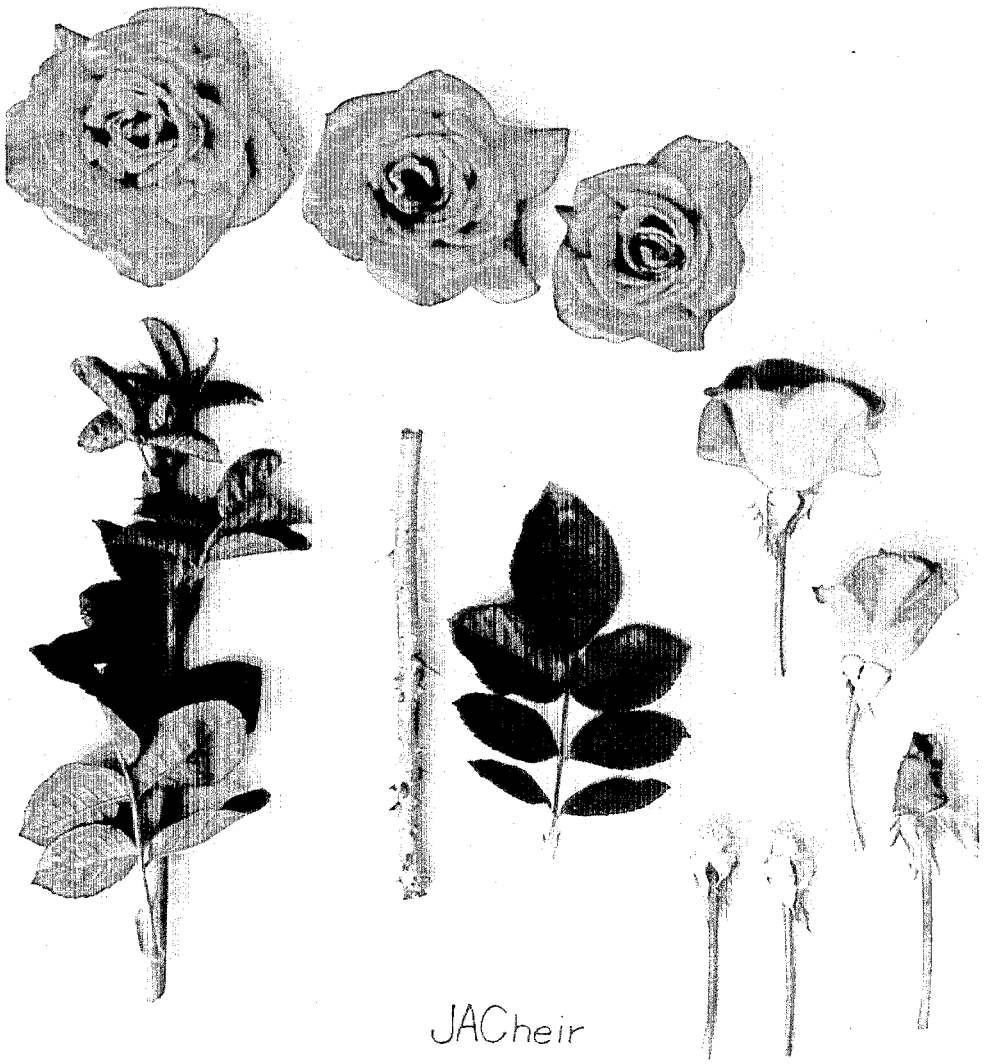
JACheir